United States Patent [19]

Moscona et al.

[11] Patent Number: 6,090,774
[45] Date of Patent: Jul. 18, 2000

[54] SINGLE PHASE LIQUID MIXTURE OF BENZOPHENONE AND MIXTURE OF AT LEAST TWO OTHER NORMALLY SOLID PERFUMERY SUBSTANCES AND PERFUMERY USES THEREOF

[75] Inventors: Murray Moscona, Rumson; Mark A. Sprecker, Sea Bright; Richard A. Weiss, Livingston, all of N.J.

[73] Assignee: International Flavors & Fragrances Inc., New York, N.Y.

[21] Appl. No.: 09/169,994

[22] Filed: Oct. 13, 1998

[51] Int. Cl.[7] .............................. A61K 7/46; C11D 3/50; C11D 9/44; C08J 3/40; C08L 3/40
[52] U.S. Cl. ............................ 512/20; 512/21; 512/25; 512/26; 510/101; 524/1
[58] Field of Search ................................. 512/20, 21, 25, 512/26; 510/101; 524/1

[56] References Cited

U.S. PATENT DOCUMENTS

| | | | |
|---|---|---|---|
| 4,650,603 | 3/1987 | Sprecker | 252/522 |
| 5,518,997 | 5/1996 | Hofstetter et al. | 512/2 |
| 5,891,833 | 4/1999 | Wei et al. | 510/121 |

FOREIGN PATENT DOCUMENTS

3922299C1  4/1991  Germany .

*Primary Examiner*—Cynthia Harris
*Assistant Examiner*—Monique T. Cole

[57] ABSTRACT

Described is a single phase liquid mixture of benzophenone and a mixture of at least two other normally solid perfumery substances which mixture contains from about 25% up to about 60% by weight of benzophenone and from about 60% down to about 25% by weight of a mixture of normally crystalline perfumery ingredients, each of which has a melting point of between about 35° C. and about 120° C. at about 1 atmosphere pressure, containing at least two substances of the following classes:

(i) coumarin derivatives;
(ii) vanillin derivatives;
(iii) resorcylic acid derivatives;
(iv) methylene dioxybenzene derivatives;
(v) trichloro-α-phenylethyl esters;
(vi) polycyclic musks;
(vii) aryl alkanoic acids; and
(viii) p-oxoalkylphenols and uses of such mixtures in augmenting or enhancing the aroma of perfume compositions, colognes and perfumed articles, including but not limited to solid or liquid anionic, cationic, nonionic or zwitterionic detergents, fabric softener compositions, fabric softener articles, hair preparations, cosmetic powders and perfumed polymers.

8 Claims, 2 Drawing Sheets

FIG. 1

SINGLE PHASE LIQUID MIXTURE OF BENZOPHENONE AND MIXTURE OF AT LEAST TWO OTHER NORMALLY SOLID PERFUMERY SUBSTANCES AND PERFUMERY USES THEREOF

BACKGROUND OF THE INVENTION

This invention relates to a single phase liquid mixture of benzophenone and mixture of at least two other normally solid perfumery substances. Furthermore, this invention relates to a novel method of preparing homogeneous benzophenone-containing liquid mixtures of solid perfume materials and the use of these mixtures for preparing solvent-free, ready made perfume formulations.

As stated in U.S. Pat. No. 5,518,997 issued on May 21, 1996, the specification for which is incorporated by reference herein, for application reasons (e.g., stability, odor intensity or substantivity), solid perfumery materials are being increasingly used in the modern perfume industry. These substances are indispensible in particular for perfumes for detergents and softeners, since these products are subjected to considerable stresses during preparation, in the market and subsequently during processing. The fragrance of these products is not only of decisive importance in decisions for or against the purchase of a certain product, but also accompanies the product from production through storage to use. In addition, the laundry which has been washed or treated with a softener must have a pleasant odor, even after weeks of storage, in order to meet the high quality expectations of the buyer of a branded article.

Furthermore, as stated in U.S. Pat. No. 5,518,997, for mixing perfume materials, the chemically stable, liquid components are usually initially introduced, as a rule with the addition of further solvents, such as dipropylene glycol or diethyl phthalate, and the solid components are added gradually with vigorous stirring, the mixture being heated externally or by means of internal heating coils until the solids melt or go into solution. Since the heating surfaces are required to be heated to relatively high temperatures in order to achieve sufficient heat transport, a certain amount of damage occurs at these heating surfaces as a result of overheating, particularly in the case of sensitive substances. Moreover, the vigorous mixing results in greater contact with air, so that it is necessary to work under an expensive inert gas atmosphere in order to avoid damage by oxidation.

Furthermore, as stated in U.S. Pat. No. 5,518,997, after dissolution of the solids, the mixture is cooled. Sensitive, readily volatile or chemically unstable materials are then added with gentle stirring, and stirring is continued until the mixture is homogeneous. This method is considerably time-consuming, since a disadvantageous solid/liquid mixing ratio is initially present, or a time-consuming heating and cooling process is necessary in between, and the use of additional solvents not only incurs costs and unnecessarily increases the processing quantities, but also additionally pollutes the environment.

U.S. Pat. No. 5,518,997 discloses a method of preparing stable liquid perfume material mixtures with a high solid content. More specifically, U.S. Pat. No. 5,518,997 discloses a method of preparing homogeneous mixtures of liquid and/or solid perfume materials by mixing the components and liquefying the mixture in which a binary or ternary eutectic premix which is liquid at room temperature and contains 10–90% of the individual substances in the case of binary mixtures and 10–70% in the case of ternary mixtures is formed from:

(a) the solid 6-acetyl-1,1,3,4,4,6-hexamethyltetrahydronaphthalene;

(b) the solid or oily α,n-hexylcinnamaldehyde (having the structure:

(c) the oily p-tert-butyl-α,n-methhylhydroinnamaldehyde (having the structure:

(d) the solid p-methoxyacetophenone (having the structure:

); and

(e) the solid benzyl o-hydroxybenzoate (having the structure:

), and the remaining solid and liquid products are introduced into this mixture simultaneously or in a sequence which is freely chosen for the particular mixture and is independent of the chemical and physical nature of the substances, and the binary and ternary eutectic premixes prepared in this manner.

In addition, U.S. Pat. No. 4,650,603 issued on Mar. 17, 1987 (the specification for which is incorporated by reference herein) discloses a single phase liquid mixture of tricyclic isochroman derivative mixture and acetyl tetrahydronaphthalene derivative mixture. More specifically, U.S. Pat. No. 4,650,603 discloses a liquid mixture of tricyclic isochroman derivatives having as a major component the compound having the structure:

and acetyl tetrahydronaphthalene derivatives having as a major component the compound having the structure:

and uses of such mixtures in augmenting or enhancing the aroma of perfume compositions, colognes and perfumed articles.

Neither of the aforementioned U.S. Pat. No. 4,650,603 or U.S. Pat. No. 5,518,997, discloses or infers the unexpectedly great versatility of the use of benzophenone in forming single phase liquid perfumery mixtures from ordinarily solid and crystalline individual components. It is particularly noteworthy that on mixing of the components with the benzophenone, the mixing occurs with an overall cooling effect (endothermic mixing) which is advantageous in utilizing heat-unstable materials.

THE INVENTION

Our invention is directed to a single phase liquid eutectic mixture which is in the liquid phase at a temperature $T_L$ above, at most, about 20° C. at about 1 atmosphere absolute pressure, satisfying the conditions:

$$T_L \geq T_{max.} \; ; \; T_{max.} \leq 20° \text{ C.}$$

where $T_{max.}$ is the temperature at the point of liquid-solid phase change, containing:
(a) from about 25% by weight up to about 60% by weight of benzophenone having the structure:

; and (b) from about 60% down to about 25% by weight of a mixture of crystalline ingredients, each of which has a melting point defined by the inequality:

$$120° \text{ C.} \geq M \geq 35° \text{ C.}$$

containing at least two substances selected from the following classes of substances:

(i) a coumarin derivative defined according to the structure:

wherein $R_1$, $R_2$, $R_3$ and $R_4$ represent hydrogen, or one of $R_1$, $R_2$, $R_3$ and $R_4$ is $C_1$–$C_3$ alkyl or $C_1$–$C_3$ alkoxy, and the other of $R_1$, $R_2$, $R_3$ and $R_4$ is hydrogen; and wherein $R_5$ and $R_5'$ represents hydrogen or one of $R_5$ and $R_5'$ is $C_1$–$C_3$ alkyl and the other of $R_5$ and $R_5'$ is hydrogen;

(ii) a vanillin derivative defined according to the structure:

wherein $R_6$ is $C_1$–$C_3$ alkyl and $R_7$ is hydrogen or $C_1$–$C_3$ alkyl;

(iii) a resorcylic acid derivative defined according to the structure:

wherein $R_8$, $R_9$ and $R_{10}$ are the same or different $C_1$–$C_3$ alkyl;

(iv) a methylene dioxybenzene derivative having the structure:

wherein $R_{11}$ is carboxaldehyde or $C_3$–$C_5$ oxoalkyl;

(v) a trichloro-α-phenylethyl ester having the structure:

wherein $R_{12}$ is $C_1$–$C_3$ alkyl;

(vi) a polycyclic musk defined according to the structure:

wherein Z is, in the alternative, one of the moieties:

and wherein one of $R_{13}$, $R_{14}$, $R_{15}$ and $R_{16}$ is acetyl and the other of $R_{13}$, $R_{14}$, $R_{15}$ and $R_{16}$ are hydrogen or $C_1$–$C_4$ lower alkyl or $R_{14}$ and $R_{15}$ complete an alkyl substituted or unsubstituted alkylenyloxyalkylene moiety containing from 3 up to 6 carbon atoms and $R_{13}$ and $R_{16}$ are hydrogen or methyl; wherein $R_{17}$, $R_{18}$, $R_{19}$, $R_{20}$, $R_{21}$, $R_{22}$, $R_{18}'$ and $R_{21}'$ are the same or different hydrogen, methyl or ethyl;

(vii) an aryl alkanoic acid defined according to the structure:

wherein N is 0 or 1 and Q is $C_2$–$C_4$ alkenylene when N is 1;

(viii) a β-naphthyl ether defined according to the structure:

wherein $R_{24}$ is $C_1$–$C_3$ alkyl; and (ix) a p-oxoalkylphenol defined according to the structure:

Our invention is also directed to the use of such mixtures in augmenting, enhancing or imparting an aroma in or to perfume compositions, colognes and perfumed articles, including but not limited to solid or liquid anionic, cationic, nonionic or zwitterionic detergents, fabric softener compositions, fabric softener articles, hair preparations, cosmetic powders and perfumed polymers.

The preferred coumarin derivatives are coumarin having the structure:

having a melting point of 68° C.; 5-ethyl coumarin having the structure:

having a melting point of 70° C.; and MARANIOL® (trademark of Givaudan-Roure S.A. of Basel, Switzerland) having the structure:

with a melting point of 114° C.

Preferred vanillin derivatives useful in the practice of our invention are: ethyl vanillin having the structure:

having a melting point of 65° C. and vanillin having the structure:

having a melting point of 83° C. The preferred resorcylic acid derivative is VERAMOSS® (trademark of International Flavors & Fragrances Inc. of New York, N.Y., U.S.A.) having the structure:

A preferred methylene dioxybenzene derivative is heliotropin having the structure:

and having a melting point of 37° C.

A preferred trichloro-α-phenylethyl ester is ROSETONE™ (trademark of International Flavors & Fragrances Inc.) having the structure:

and a melting point of 88° C.

Preferred polycyclic musks useful in the practice of our invention are as follows:

(a) CELESTOLIDE® (registered trademark of International Flavors & Fragrances Inc.) having the structure:

and a melting point of 76° C.;

(b) TONALID® (registered trademark of Hercules, Inc. of Wilmington, Del.), a mixture of compounds having the structures:

; and

;

(c) GALAXOLIDE® (registered trademark of International Flavors & Fragrances Inc.), a mixture of compounds having the structures:

;

;

;

-continued

; and

Preferred aryl alkanoic acids useful in the practice of our invention are:

(a) benzoic acid having the structure:

; and (b) cinnamic acid having the structure:

The preferred β-naphthoether useful in the practice of our invention is "yara yara" having the structure:

and a melting point of 73° C.

The p-oxoalkylphenol used in the practice of our invention is OXYPHENYLON™ (trademark of International Flavors & Fragrances Inc.) having the structure:

and a melting point of 82° C.

An additional methylenedioxybenzene derivative preferred in the practice of our invention is DULCINYL™ (trademark of International Flavors & Fragrances Inc.) having the structure:

and a melting point of 43° C.

Preferred mixtures including their ranges of weight percents useful in the practice of our invention are as follows:

| Ingredient | Range of Weight Percentages |
| --- | --- |
| Coumarin | 6–30% |
| Ethyl vanillin | 8–15% |
| Heliotropin | 7–15% |
| VERAMOSS ® | 0–40% |
| Benzophenone | 25–60% |
| Benzoic acid | 0–12% |
| CELESTOLIDE ® | 0–40% |
| TONALID ® | 0–40% |
| GALAXOLIDE ® | 0–40% |
| OXYPHENYLON ™ | 0–2% |
| DULCINYL ™ | 0–2% |

It is important to note that on preparing the aforementioned mixtures, a cooling effect occurs, that is the energy of mixing causes a reduction in the temperature of the mixture. This temperature reduction is advantageous in that certain temperature-sensitive materials are not exposed to excessive heat. Furthermore, the entire mixture is not exposed to excessive heat which occurs in other procedures in preparing perfumes. This cooling effect is unexpected and advantageous in preparing the mixtures of our invention.

The liquid mixture containing benzophenone of our invention and one or more auxiliary perfume ingredients including alcohols, aldehydes, nitriles, esters, cyclic esters, ketones, ethers, natural essential oils and synthetic essential oils may be admixed so that the combined odors of the individual components produce a pleasant and desired fragrance. Such perfume compositions usually contain:

(a) the main note or the "bouquet" or foundation stone of the composition;

(b) modifiers which round off and accompany the main note;

(c) fixatives which include odorous substances which lend a particular note to the perfume throughout all stages of evaporation and substances which retard evaporation; and (d) topnotes which are usually low-boiling, fresh smelling materials.

In perfume compositions, it is the individual components which contribute to its particular olfactory characteristics, but the overall effect of the perfume composition will be the sum of the effects of each of the ingredients. Thus, the liquid benzophenone-containing mixture of our invention and one or more auxiliary perfume ingredients can be used to alter the aroma characteristics of a perfume composition, for example, by utilizing or moderating the olfactory reaction contributed by a least one other ingredient in the composition.

The amount of liquid benzophenone-containing mixture of our invention and one or more auxiliary perfume ingredients of our invention can range up to 100% of the fragrance components employed in a perfume article and can range up to 10% of the weight of the perfumed article and will depend upon considerations of cost, nature of the end product, the effect desired on the finished product and the particular fragrance sought.

The liquid benzophenone-containing mixture of our invention and one or more perfume ingredients are useful, taken alone or in perfume compositions as olfactory components in anionic, cationic and nonionic detergents, soaps, fabric softener compositions, fabric softener articles for use in clothes dryers (e.g., BOUNCE®, a registered trademark of the Procter & Gamble Company of Cincinnati, Ohio), space odorants and deodorants, perfumes, colognes, toilet water, bath preparations, such as lacquers, brilliantines, creams, deodorants, hand lotions and sun screens; powders such as talcs, dusting powders, face powders and the like. When used as an olfactory component in perfume compositions or in a perfumed article such as anionic, nonionic, cationic and zwitterionic detergents and in fabric softener compositions and fabric softener articles, as little as 0.05% of the liquid benzophenone mixture of our invention and one or more auxiliary perfume ingredients will suffice to impart a fragrance, such as a musk fragrance. Generally no more than 10% of the liquid benzophenone-containing mixture of our invention and one or more auxiliary perfume ingredients based on the ultimate end product is required in a perfumed article.

The benzophenone-containing liquid composition of our invention can also be used in a carrier and can be encapsulated in such a carrier. Such a carrier can be an absorbent solid such as a gum (e.g., gum arabic or xanthan gum) or components for encapsulating the composition are exemplified by gelatin which is used in coacervation processes.

It will thus be apparent that the benzophenone-containing liquid mixture of our invention and one or more auxiliary perfume ingredients (if desired) can be used to alter the sensory properties, particularly organoleptic properties of a wide variety of consumable fragranced materials.

BRIEF DESCRIPTION OF THE DRAWINGS

FIG. 1 is a phase diagram plotting melting point in degrees Centigrade versus percent of benzophenone in the mixture which also contains the following substances:

5 parts coumarin;

6 parts ethyl vanillin;

5 parts heliotropin; and 15 parts VERAMOSS®.

DETAILED DESCRIPTION OF THE DRAWINGS

Figure 1:
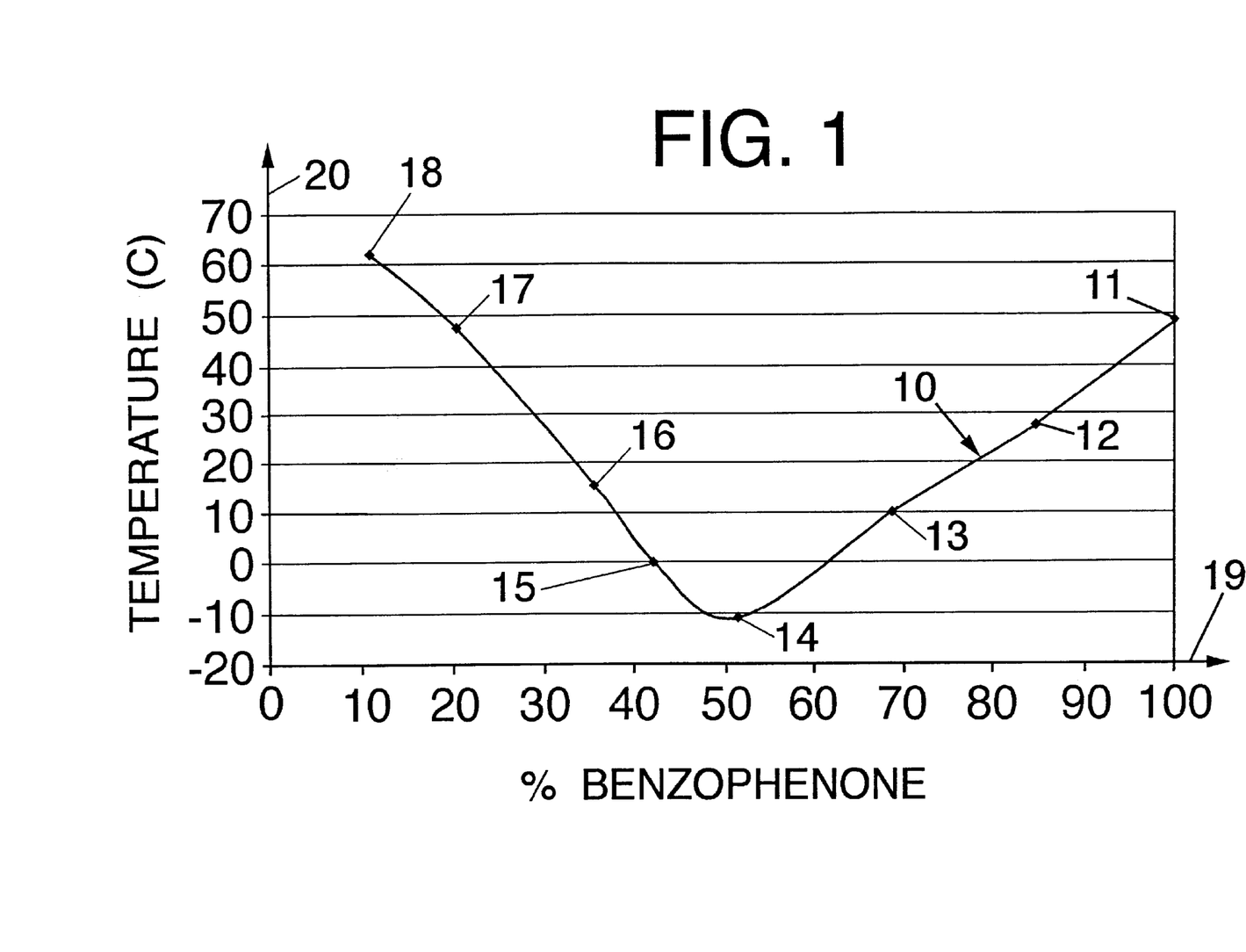

FIG. 1 is a plot showing melting point and degrees Centigrade versus percent benzophenone in a mixture which also includes:

5 parts by weight coumarin;

6 parts by weight ethyl vanillin;

5 parts by weight heliotropin; and 15 parts by weight VERAMOSS®

The percent benzophenone is shown on the X axis, which X axis is indicated by reference numeral 19. The melting point is shown on the Y axis, which Y axis is indicated by reference numeral 20. The graph showing phase separation is indicated by reference numeral 10, with the eutectic point indicated by reference numeral 14.

The data point indicated by reference numeral 11 is for 100% benzophenone and no other components of the mixture. The data point indicated by reference numeral 12 is for 85% benzophenone. The data point indicated by reference numeral 13 is for 70% benzophenone. The data point (eutectic) indicated by reference numeral 14 is for 51.5% benzophenone, with the resultant mixture having a melting point of −12° C. The data point indicated by reference numeral 15 is for 42% benzophenone. The data point indicated by reference numeral 16 is for 36% benzophenone. The data point indicated by reference numeral 17 is for 21% benzophenone. The data point indicated by reference numeral 18 is for a mixture containing 11.4% benzophenone.

Figures 2, 3:
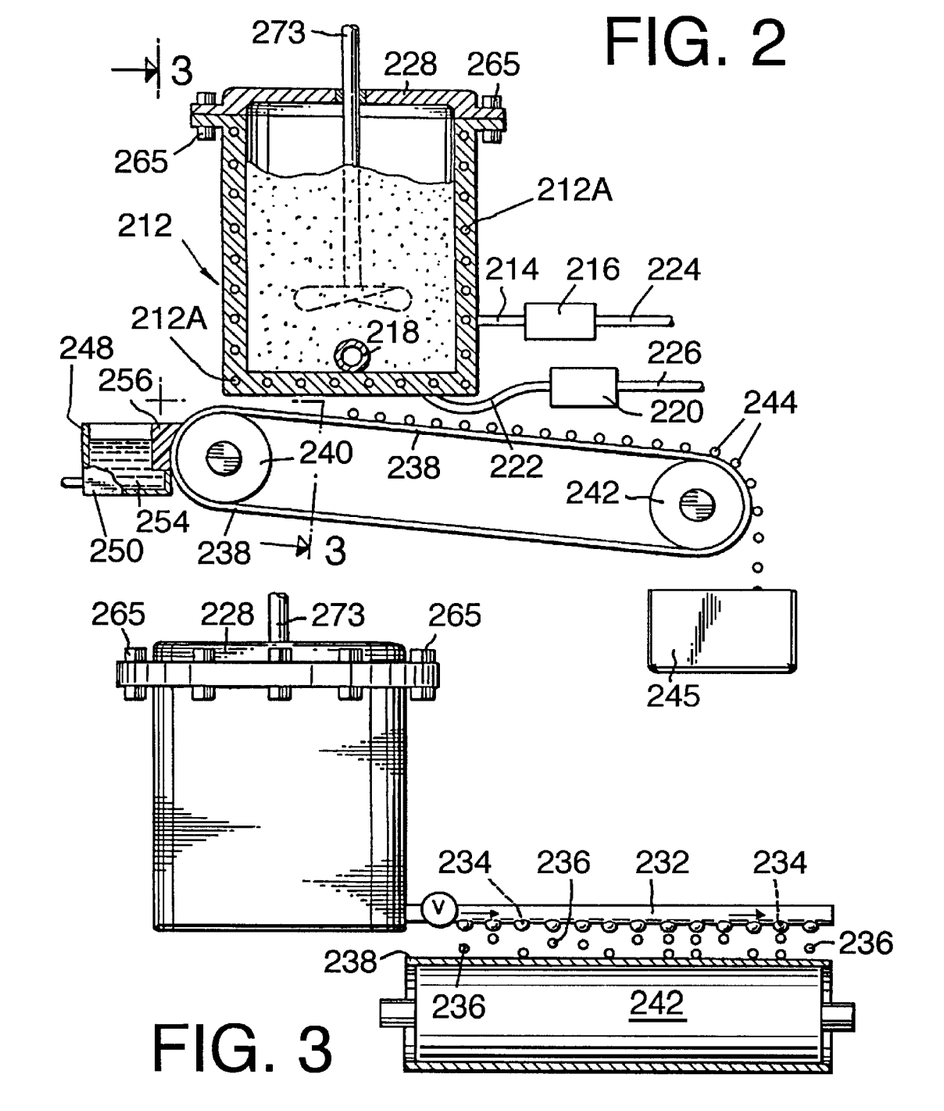
FIG. 2 represents a cutaway side elevation view of apparatus used in forming perfumed polymers, containing a liquid single phase benzophenone-containing mixture of our invention.
FIG. 3 is a front view of the apparatus of FIG. 2, looking in the direction of the arrows.

Referring to FIGS. 2 and 3, there is provided a process for forming scented polymer elements (wherein the polymer may be a thermoplastic polymer such as low density polyethylene or polypropylene or copolymers of ethylene-vinyl acetate or mixtures of a polymer and a copolymer such as a copolymer of ethylene-vinyl acetate and polyethylene), such as pellets useful in the formation of plastic particles useful in fabricating certain articles which may be perfumed. The process comprises heating the polymer or mixture of polymers to the melting point of said polymer or mixture of polymers, e.g., 250° C. in the case of low density polyethylene. The lower-most portion of the container is maintained at a slightly lower temperature, and the material of the container is taken off at such location for delivery through the conduit. Thus, referring to FIGS. 2 and 3 in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymers and a perfuming substance containing the benzophenone liquid mixture of our invention is placed. The container is closed by means of an airtight lid 228, and the lid is clamped to the container by airtight bolts 265. A stirrer 273 traverses the lid or cover 228 in an airtight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 Saybolt seconds. The heater is operated to maintain the upper portion of the container 212 within a temperature range of, for example, 250° C. in the case of low density polyethylene. The bottom portion of the container 212 is heated by means of heating coils 212A, regulated through the control 220, connected thereto through a connecting wire 222 to maintain the lower portion of the container 212 within a temperature range of 225–240° C.

Thus, the polymer or mixture of polymers added to the container 212 is heated from 10–12 hours, whereafter the perfume composition or perfume material containing the liquid benzophenone-containing mixture of our invention is quickly added to the melt. Generally, about 10–45% by weight of the resulting mixture of the perfumery substance is added to the polymer.

After the perfume material is added to the container 212, the mixture is stirred for a few minutes, for example, 5–15 minutes, and maintained within the temperature ranges indicated previously by the heating coil 212A. The controls 216 and 220 are connected through cables 224 and 226 to a suitable supply of electric current for supplying the power for heating purposes.

Thereafter, the valve V is opened permitting the mass to flow outwardly through conduit 232 (also indicated by reference numeral 218 in FIG. 2) having a multiplicity of orifices 234 adjacent to the lower side thereof. The outer end of the conduit 232 is closed so that the liquid polymer intimately admixed with the perfume substance containing the benzophenone-containing liquid mixture of our invention will continuously drop through the orifices 234 downwardly from the conduit 232. During this time, the temperature of the polymer intimately admixed with the perfumery substance in the container 212 is accurately controlled so that a temperature in the range of from about 240–250° C. (in the case of low density polyethylene) will exist in the conduit 232. The regulation of the temperature through the control 216 and 220 is essential in order to insure temperature balance to provide for the continuous dropping or dripping of molten polymer intimately admixed with the perfume substance containing the benzophenone-containing liquid mixture of our invention through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 245 which is advantageously filled with water or some other suitable cooling liquid to insure the rapid cooling of each of the pellets 244. The pellets 244 are then collected from the container 245 and utilized for formation of other functional products, e.g., garbage bags and the like. The belt 238 is continuously cooled by means of the cooling liquid contained in container 250 having sidewall 248 and containing a cooling liquid transmission element, e.g., a sponge indicated by reference numeral 256, with the cooling fluid, e.g., cold water indicated by reference numeral 254. The sponge 256 transmits the cooling liquid to the belt 238 to keep the belt cool so that the polymer containing the benzophenone-containing liquid is solidified with the benzophenone-containing liquid contained within the interstices of the polymer.

The following examples are illustrative, and the invention is to be considered restricted thereto only as indicated in the appended claims. All parts and percentages given herein are by weight unless otherwise specified.

EXAMPLE I

PREPARATION OF LIQUID EUTECTIC FRAGRANCE MIXTURES

The following mixtures are prepared, each of which form eutectic liquid compositions at temperatures indicated in the following examples. Each of the mixtures, when admixed, gives rise to a cooling effect resulting from the endothermic energy of mixing:

|  | Weight % of Ingredient in Composition | | | | |
| --- | --- | --- | --- | --- | --- |
| Ingredients | IA | IB | IC | ID | IE |
| Coumarin | 10.31 | 10.31 | 10.31 | 10.31 | 0 |
| Ethyl vanillin | 12.37 | 12.37 | 12.37 | 12.37 | 0 |
| Heliotropin | 10.31 | 10.31 | 10.31 | 10.31 | 0 |

-continued

|  | Weight % of Ingredient in Composition | | | | |
| --- | --- | --- | --- | --- | --- |
| Ingredients | IA | IB | IC | ID | IE |
| VERAMOSS ® | 20.62 | 0 | 10.31 | 10.31 | 0 |
| Benzoic acid | 10.31 | 0 | 0 | 0 | 0 |
| Benzophenone | 36.08 | 36.08 | 36.08 | 36.08 | 33.3 |
| CELESTOLIDE ® | 0 | 30.93 | 20.62 | 0 | 0 |
| TONALID ® | 0 | 0 | 0 | 20.62 | 33.3 |
| GALAXOLIDE ® | 0 | 0 | 0 | 0 | 33.3 |

The eutectic temperature for Example IA is –15° C. The eutectic temperature for Example IB is 3° C. The eutectic temperature for Example IC is –13° C. The eutectic temperature for Example ID is –17° C. The eutectic temperature for Example IE is –4° C. The perfume composition of Example IA has an intense floral, chypre aroma with moss undertones. The perfume compositions of Example IB, IC and ID have floral, chypre aromas with moss and musky undertones. The perfume composition of Example IE has an intense musk aroma with animalic undertones.

EXAMPLE II

PREPARATION OF LIQUID EUTECTIC FRAGRANCE MIXTURES

The following mixtures are prepared, each of which form eutectic liquid compositions at temperatures indicated in the following examples. Each of the mixtures, when admixed, gives rise to a cooling effect resulting from the endothermic energy of mixing:

|  | Weight % of Ingredient in Composition | | | | |
| --- | --- | --- | --- | --- | --- |
| Ingredients | IIA | IIB | IIC | IID | IIE |
| Coumarin | 7.8 | 18.69 | 25.64 | 11.49 | 9.35 |
| Ethyl vanillin | 9.38 | 11.21 | 10.26 | 13.79 | 11.21 |
| Heliotropin | 7.8 | 9.35 | 8.55 | 11.49 | 9.35 |
| VERAMOSS ® | 23.44 | 28.04 | 25.64 | 22.99 | 37.38 |
| Benzophenone | 51.56 | 32.71 | 29.91 | 40.23 | 32.71 |

The eutectic point for the composition of Example IIA is –12° C. The eutectic point for the composition of Example IIB is 1° C. The eutectic point for the composition of Example IIC is –11° C. The eutectic point for the composition of Example IID is –13° C. The eutectic point for the composition of Example IIE is 21° C.

Each of the perfume compositions of Examples IIA, IIB, IIC, IID and IIE have floral, chypre aromas with intense moss undertones.

EXAMPLE III

PREPARATION OF A SOAP COMPOSITION

100 Grams of soap chips are admixed with 1 gram of one of the perfume compositions of Table I below until a substantially homogeneous composition is obtained. The perfumed soap manifests an excellent aroma as set forth in Table I below:

TABLE I

| Perfume Ingredients | Aroma |
|---|---|
| Benzophenone-containing liquid mixture of Example IA | Intense floral, chypre aroma with moss undertones. |
| Benzophenone-containing liquid mixture of Example IB | Floral, chypre aroma with moss and musky undertones. |
| Benzophenone-containing liquid mixture of Example IC | Floral, chypre aroma with moss and musky undertones. |
| Benzophenone-containing liquid mixture of Example ID | Floral, chypre aroma with moss and musky undertones. |
| Benzophenone-containing liquid mixture of Example IE | Intense musk aroma with animalic undertones. |
| Benzophenone-containing liquid mixture of Example IIA | Floral, chypre aroma with intense moss undertones. |
| Benzophenone-containing liquid mixture of Example IIB | Floral, chypre aroma with intense moss undertones. |
| Benzophenone-containing liquid mixture of Example IIC | Floral, chypre aroma with intense moss undertones. |
| Benzophenone-containing liquid mixture of Example IID | Floral, chypre aroma with intense moss undertones. |
| Benzophenone-containing liquid mixture of Example IIE | Floral, chypre aroma with intense moss undertones. |

EXAMPLE IV

PREPARATION OF A COLOGNE AND HANDKERCHIEF PERFUME

One of the perfume substances as set forth in Table I of Example III is incorporated into a cologne at concentrations 1.5%, 2.0%, 2.5%, 3.0%, 3.5% and 4.0% in 80%, 85%, 90% and 95% aqueous ethanol; and into handkerchief perfumes at concentrations of 15%, 20%, 25% and 30% (in 85%, 90% and 95% aqueous ethanol). Distinct and definite fragrances as set forth in Table I of Example III are imparted to the cologne and to the handkerchief perfume at each of the levels indicated.

EXAMPLE V

PREPARATION OF A COSMETIC POWDER COMPOSITION

A cosmetic powder is prepared by mixing in a ball mill 100 grams of talcum powder with 0.15 grams of one of the substances of Table I of Example III. The resulting powders have excellent floral, chypre aromas.

EXAMPLE VI

Utilizing the procedure of Example I of column 15 of U.S. Pat. No. 3,632,396 (the specification for which is incorporated herein by reference), a non-woven cloth substrate useful as a dryer-added fabric softening article of manufacture is prepared wherein the substrate, the substrate coating, the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):

57% $C_{20\text{-}22}$HAPS;
22% isopropyl alcohol;
20% antistatic agent; and
1% of one of the perfume substances of Table I of Example III.

Fabric softening compositions prepared as set forth above, having an aroma characteristic as set forth in Table I of Example III essentially consists of a substrate having a weight of about 3 grams per 100 square inches; a substrate coating of about 1.85 grams per 100 square inches of substrate; and an outer coating of about 1.4 grams per 100 square inches of substrate, thereby providing a total aromatized substrate and an outer coating weight ratio of about 1:1 by weight of the substrate. Aromas are imparted as set forth in Table I of Example III in a pleasant manner to the head space in the dryer on operation thereof, using the said dryer-added fabric softening, non-woven fabric.

EXAMPLE VII

PREPARATION OF A SOAP COMPOSITION

100 Grams of soap chips are prepared according to Example V of U.S. Pat. No. 4,058,490 issued on Nov. 15, 1977, the specification for which is incorporated by reference herein, as follows:

"The sodium salt of an equal mixture of $C_{10}$–$C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 5.0 by the addition of a small amount of a 50% aqueous solution of NaOH. The isopropanol is distilled off and the remaining aqueous solution is dried. The resulting solid actives are then blended in a chip mixer with 10 lbs. water, 0.2 lb. titanium hydroxide."

The resulting blend is then mixed with one of the perfume substances of Table I of Example III until a substantially homogeneous composition is obtained. The perfumed soap composition manifests an aroma as set forth in Table I of Example III.

EXAMPLE VIII

GRANULAR DETERGENT COMPOSITION

A granular detergent composition is prepared according to United Kingdom Patent No. 1,501,498, the specification for which is incorporated by reference herein, having the following formula. It is prepared by spray-drying the following mixture:

| Ingredient | Parts by Weight |
|---|---|
| Sodium salt of ethoxylated fatty alcohol sulfate having an average of about 2.25 moles of ethylene oxide per mole of fatty alcohol | 14.1 |
| Sodium tallow alkyl sulfate | 2.4 |
| Sodium silicate solids ratio: $SiO_2/Na_2O$ = 2.0 | 6.0 |
| Sodium tripolyphosphate | 24.0 |
| $Na_{12}(AlO_2.SiO_2).27H_2O$ | 18.0 |
| Moisture | 10.0 |
| Sodium sulfate | 25.0 |
| Perfume substance of Table I of Example III | 4.0 |

Laundry solutions containing the above detergent compositions are used to launder fabrics. Each of the laundry compositions, both prior to and on laundering, give rise to a pleasant aroma as set forth in Table I of Example III.

EXAMPLE IX

PERFUMED LIQUID DETERGENT

Concentrated liquid detergents are prepared with aromas as set forth in Table I of Example III containing 0.10%, 0.15% and 0.20% of each of the substances of Table I of Example III in the liquid detergent. The liquid detergent is a builder-free liquid detergent consisting of (a) 50% of a nonionic surfactant having an HLB of 8.0 and a critical micelle concentration of 0.007 weight percent at 25° C.; and (b) an anionic surfactant which is a triethanolamine prepared according to United Kingdom Patent No. 1,491,603, the specification for which is incorporated by reference herein.

The detergents all possess aromas as set forth in Table I of Example III, supra.

EXAMPLE X

PREPARATION OF A DETERGENT COMPOSITION

A total of 100 grams of detergent powder (a low phosphate content detergent composition which contains 12% by weight phosphate builder, 8% hardness mineral ion insensitive detergent, 0.9% by weight maleic anhydride-vinyl compound copolymer and 2% alkylene oxide condensation product prepared according to Example IV at column 9 of U.S. Pat. No. 4,000,080 issued on Dec. 28, 1976, the specification for which is incorporated by reference herein) is intimately admixed with 0.15 grams of one of the perfume materials of Table I of Example III, supra, until a substantially homogeneous composition is obtained. The composition has an aroma as set forth in Table I of Example III, supra.

EXAMPLE XI

Each of the fragranced materials of Table I of Example III, supra, are added to a 50:50 weight:weight mixture of low density polyethylene:polyepsilon caprolactone PCL-700 forming pellets with scents as set forth in Table I of Example III, supra.

75 Pounds of a mixture of PCL-700 polyepsilon caprolactone (manufactured by the Union Carbide Corporation of New York, N.Y., having a melting point of about 180–190° F.):low density polyethylene are heated to about 250° C. in a container of the kind illustrated in FIGS. 2 and 3. 25 Pounds of each of the fragrance materials as set forth in Table I of Example III are then quickly added to the liqufied polymer mixture, the lid 228 is put in place and the agitating means 273 are actuated. The temperature is then raised to about 260° F., and the mixing is continued for 5–15 minutes. The valve V is then opened to allow flow of the molten polymer enriched with perfume ingredient to exit through the orifices 234. The liquid falling through the orifices 234 solidifies almost instantaneously upon impact with the moving cooled conveyor 238. Polymer beads or pellets 244 have pronounced scents as described in Table I of Example III, supra, are thus formed. Analysis demonstrates that the pellets contain about 25% of the perfume material so that almost no losses in the scenting substance did occur. These pellets may be called "master pellets."

50 Pounds of each batch of the scent containing "master pellets" are then added to 1,000 pounds of unscented polypropylene, and the mass is heated to the liquid state. The liquid is molded into thin sheets of films. The thin sheets of films have pronounced aromas as set forth in Table I of Example III, supra. The sheets of films are cut into strips of 0.25 inches in width×3 inches in length and placed into room air fresheners.

On operation of the room air freshener, after 4 minutes, the room in each case has an aesthetically pleasing aroma with no foul odor being present, the aroma being described in Table I of Example III, supra.

What is claimed is:

1. A single phase liquid eutectic mixture which is in the liquid phase at a temperature $T_L$ above, at most, about 20° C. and at about 1 atmosphere absolute pressure, satisfying the conditions:

$$T_L \geq T_{max.} \; ; \; T_{max.} \leq 20° C.$$

wherein $T_{max.}$ is the temperature of the point of liquid-solid phase change, containing the following ingredients in the following percentage ranges:

(a) coumarin having the structure:

- 6–30%;

(b) ethyl vanillin having the structure:

- 8–15%;

(c) heliotropin having the structure:

- 7–15%;

(d) the compound having the structure:

- 0–40%;

(e) benzophenone having the structure:

- 25–60%;

(f) benzoic acid having the structure:

- 0–12%;

(g) the compound having the structure:

- 0–40%;

(h) a mixture of compounds having the structures:

- 0–40%;

(i) a mixture of compounds having the structures:

; and

- 0–40%;

(j) the compound having the structure:

- 0–2%; and (k) the compound having the structure:

- 0–2%.

2. The composition of claim 1 containing the ingredients:

| | |
|---|---|
| coumarin | 10.31% |
| ethyl vanillin | 12.37% |
| heliotropin | 10.31% |
| the compound having the structure:  | 30.93% |
| benzophenone | 36.08% |

3. The composition of claim 1 containing the following ingredients:

| | |
|---|---|
| coumarin | 7.8% |
| ethyl vanillin | 9.38% |
| heliotropin | 7.8% |
| the compound having the structure: | 23.44% |

| | |
|---|---|
| benzophenone | 51.56% |

4. The composition of claim 1 containing the following ingredients:

| | |
|---|---|
| coumarin | 10.31% |
| ethyl vanillin | 12.37% |
| heliotropin | 10.31% |
| the compound having the structure: | 30.93% |

| | |
|---|---|
| benzophenone | 36.08% |

5. The composition of claim 1 containing the following ingredients:

| | |
|---|---|
| coumarin | 10.31% |
| ethyl vanillin | 12.37% |

-continued

| | |
|---|---|
| heliotropin | 10.31% |
| the compound having the structure: | 20.62% |

| | |
|---|---|
| the compound having the structure: | 10.31% |

| | |
|---|---|
| benzophenone | 36.08% |

6. A process for augmenting or enhancing the aroma of a perfume composition comprising the step of adding to said perfume composition an aroma augmenting or enhancing quantity of the composition of matter defined according to claim 1.

7. A process for augmenting or enhancing the aroma of a liquid anionic, nonionic, cationic or zwitterionic detergent comprising the step of intimately admixing with said liquid anionic, nonionic, cationic or zwitterionic detergent an aroma augmenting or enhancing quantity of the composition of matter defined according to claim 1.

8. A process for augmenting or enhancing the aroma of a thermoplastic polymer comprising the step of intimately admixing with said thermoplastic polymer in the liquid state an aroma augmenting or enhancing quantity of the composition of matter defined according to claim 1.

* * * * *